(12) United States Patent
van der Heiden et al.

(10) Patent No.: US 8,889,406 B2
(45) Date of Patent: Nov. 18, 2014

(54) METHOD AND APPARATUS FOR CULTIVATING CELLS UTILIZING WAVE MOTION

(75) Inventors: Pieter van der Heiden, Wouwse-Plantage (NL); Marc Buevink, Doetinchem (NL); Nicolaas Marius Gerard Oosterhuis, Rolde (NL)

(73) Assignee: Strix Beheer B.V. (NL)

( * ) Notice: Subject to any disclaimer, the term of this patent is extended or adjusted under 35 U.S.C. 154(b) by 1446 days.

(21) Appl. No.: 11/964,874

(22) Filed: Dec. 27, 2007

(65) Prior Publication Data

US 2008/0160597 A1 Jul. 3, 2008

Related U.S. Application Data

(63) Continuation of application No. PCT/NL2006/000319, filed on Jun. 27, 2006.

(30) Foreign Application Priority Data

Jun. 29, 2005 (EP) ..................... 05076493

(51) Int. Cl.
| | |
|---|---|
| *C12M 1/00* | (2006.01) |
| *C12M 3/00* | (2006.01) |
| *B01F 11/00* | (2006.01) |
| *B01F 13/10* | (2006.01) |
| *C12M 3/06* | (2006.01) |
| *C12M 1/42* | (2006.01) |

(52) U.S. Cl.
CPC ............ *C12M 23/14* (2013.01); *B01F 11/0025* (2013.01); *B01F 13/1013* (2013.01); *B01F 13/1022* (2013.01); *C12M 27/16* (2013.01); *C12M 35/04* (2013.01)
USPC .................... 435/289.1; 435/71.1; 435/252.8; 435/287.1; 435/394; 366/211; 366/215; 366/218

(58) Field of Classification Search
CPC ............ A01B 12/006; B01F 13/1022; B01F 13/1013; B01F 11/0025; B01F 11/0005; B01F 13/1025; B01F 15/00746; B01F 5/0057; B01F 5/0065; B01F 11/017; B01F 11/0008; B01F 11/0022; B01F 11/0028; B01F 9/0016; C12M 27/16; C12M 35/04; C12M 23/14; C12M 41/36; Y10S 366/605; Y10S 604/903; A61M 1/025; F16H 21/42; G01N 2035/0453; G01N 33/48
USPC ............ 366/11, 110, 211, 215–218; 435/261, 435/289.1
See application file for complete search history.

(56) References Cited

U.S. PATENT DOCUMENTS

| | | | |
|---|---|---|---|
| 5,017,490 A * | 5/1991 | Taiariol et al. | 435/401 |
| 5,697,701 A * | 12/1997 | Forrest et al. | 366/110 |
| 6,190,913 B1 | 2/2001 | Singh | |
| 2003/0036192 A1 | 2/2003 | Singh | |
| 2004/0043481 A1 | 3/2004 | Wilson | |
| 2004/0209346 A1 * | 10/2004 | Adelberg et al. | 435/261 |

FOREIGN PATENT DOCUMENTS

WO  WO 03/060061  7/2003

OTHER PUBLICATIONS

Dhanasekharan, "Design and Scale-Up of Bioreactors Using Computer Simulations," *BioProcess Intl.*, Mar. 2006, pp. 34-40.

* cited by examiner

*Primary Examiner* — Michael Marcheschi
*Assistant Examiner* — Shanta G Doe
(74) *Attorney, Agent, or Firm* — Banner & Witcoff, Ltd.

(57) ABSTRACT

An apparatus for cultivating cells utilizing wave motion comprising a container, a retaining member configured to retain the container, a drive assembly for swiveling the container with respect to the substantially horizontal pivot axis and to swivel, such that during swiveling the pivot axis follows a cyclical closed-loop path.

12 Claims, 17 Drawing Sheets

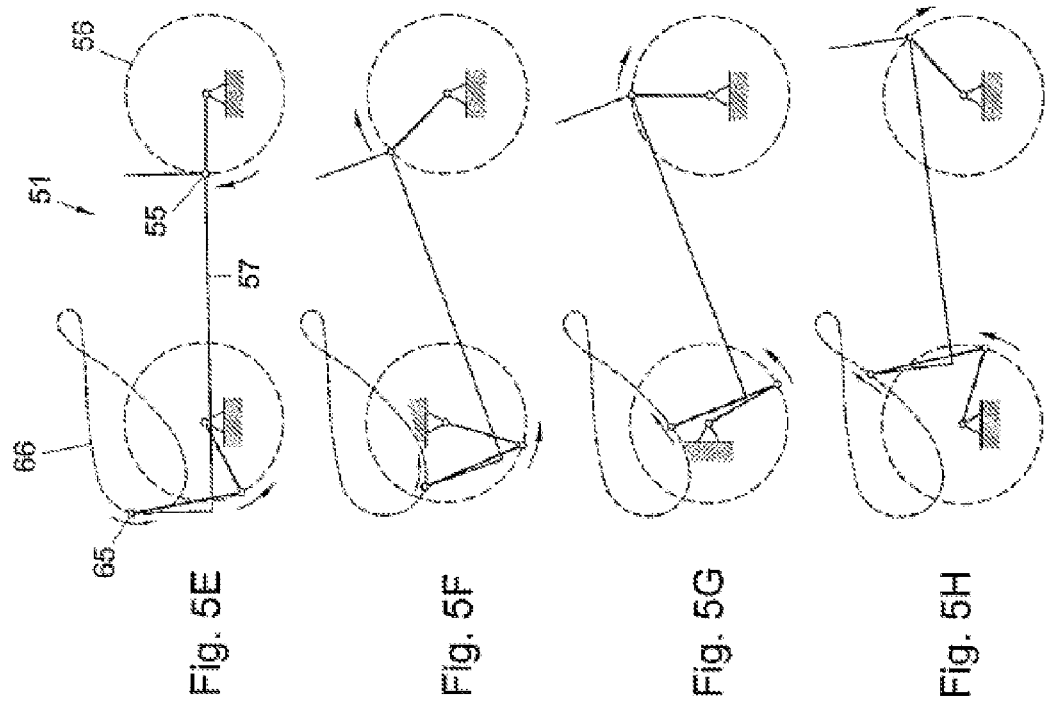
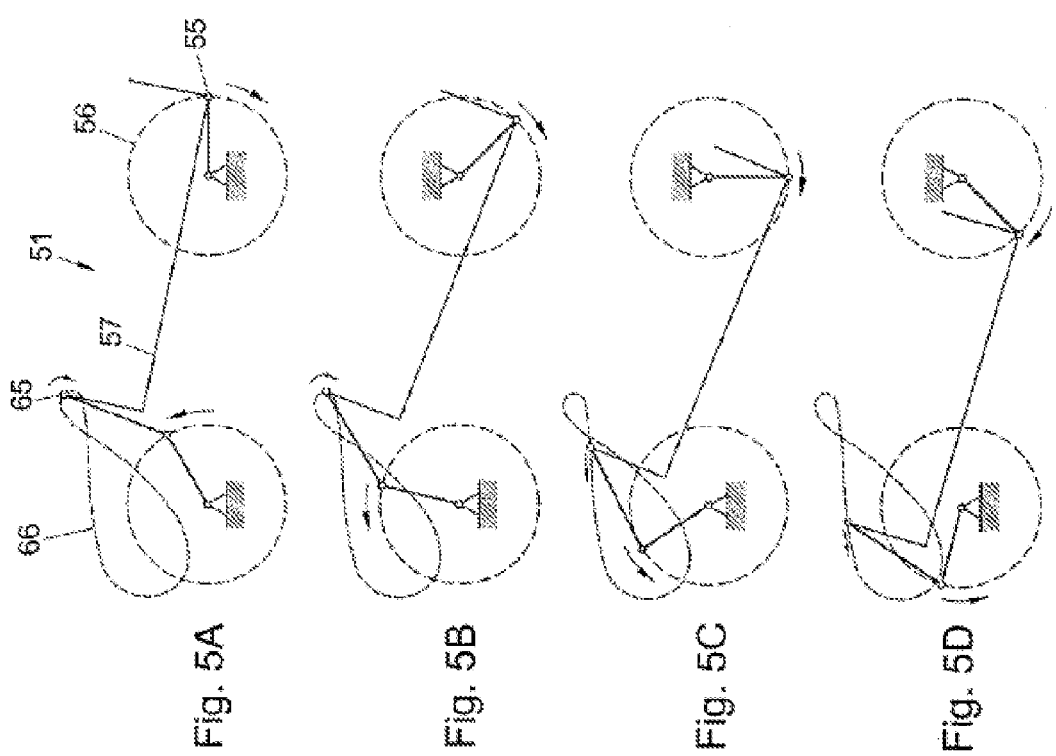

METHOD AND APPARATUS FOR CULTIVATING CELLS UTILIZING WAVE MOTION

RELATED APPLICATIONS

This application is a continuation of PCT application no. PCT/NL2006/000319, designating the United States and filed Jun. 27, 2006; which claims the benefit of the filing date of European application no. EP 05076943.5, filed Jun. 29, 2005; each of which is hereby incorporated herein by reference in its entirety for all purposes.

FIELD

The invention relates to the field of biotechnology and industrial scale cell culturing. In particular, it relates to a method and an apparatus for cultivating cells utilizing wave motion.

BACKGROUND

Such a method and such an apparatus are known from U.S. Pat. No. 6,190,913 B1. This known technique employs a pre-sterilized flexible plastic bag in which cells are cultivated. The bag is partially filled with growth media and the remainder of the bag is continuously purged with air or other oxygen-rich gas. The bag is secured to a rocking platform that is rocked to and fro about one horizontal axis by the alternate actuation of pneumatic pistons. The rocking motion promotes wave formation in the bag which provides liquid mixing and enhances oxygen transfer from the headspace gas to the liquid phase where it is essential for cell growth and metabolism. Adequate gas-liquid mass transfer (oxygen supply and carbon dioxide removal) is one of the important parameters for bioreactor design and functioning, and also plays a decisive role in strategies for upscaling culturing systems (see Dhanasekharan, K., *BioProcess Int.*, March 2006, pages 2-6).

SUMMARY

It is an object of the invention to further improve cell growth and productivity in the cultivating of cells utilizing wave motion. Inter alia, it is an object to provide a cell culturing system which is suitable for industrial scale-up.

According to the present invention, this object is achieved by providing a method for cultivating cells utilizing wave motion, comprising the steps of: providing a container; introducing a gas containing oxygen, a liquid medium and a cell culture into the container; moving the container such that the container swivels with respect to a substantially horizontal pivot axis to thereby induce a wave motion to the liquid medium in the container, which wave motion contributes to the necessary oxygen transfer and mixing required for cell growth, characterized in that during said swiveling of the container said pivot axis follows a cyclical closed-loop path. The invention may also be embodied in an apparatus for cultivating cells in a container utilizing wave motion of a liquid medium in the container, comprising retaining means for retaining the container and a driving mechanism for swiveling the container with respect to a substantially horizontal pivot axis, characterized in that the driving mechanism is arranged to swivel the container such that during said swiveling said pivot axis follows a cyclical closed-loop path. An assembly is provided for cultivating cells, comprising an apparatus for cultivating cells in a container utilizing wave motion of a liquid medium in the container, comprising retaining means for retaining the container and a driving mechanism for swiveling the container with respect to a substantially horizontal pivot axis, characterized in that the driving mechanism is arranged to swivel the container such that during said swiveling said pivot axis follows a cyclical closed-loop path; and a container for cultivating cells when retained by the retaining means of said apparatus.

The combination of the swiveling movement of the container with respect to the pivot axis and the cyclical movement of the pivot axis along the closed-loop path induces a wave motion of the liquid medium in the container, which wave motion results into enhanced oxygen transfer and liquid mixing. The wave motion can be optimized for a given cell culture to provide sufficient oxygen transfer for high-density cell culture without excessive foaming or shear damage. No mechanical mixing is required. Thus, an improved cell growth and productivity, e.g. of a recombinantly produced protein, can be achieved.

Further, the invention also comprises an improved flexible bag (container) for use in the present invention, the improvement consisting of a bag of which the volume can be changed in situ e.g., by opening or closing one or more compartments and/or a bag which has essentially straight corners.

Particular embodiments of the invention are set forth in the dependent claims.

Further features, effects and details of embodiments of the invention are described below with reference to the accompanying schematic drawings.

BRIEF DESCRIPTION OF THE DRAWINGS

FIGS. 5A-5H show the example of FIG. 4 at different stages during the movement of a container.

DETAILED DESCRIPTION OF CERTAIN PREFERRED EMBODIMENTS

Figure 1:
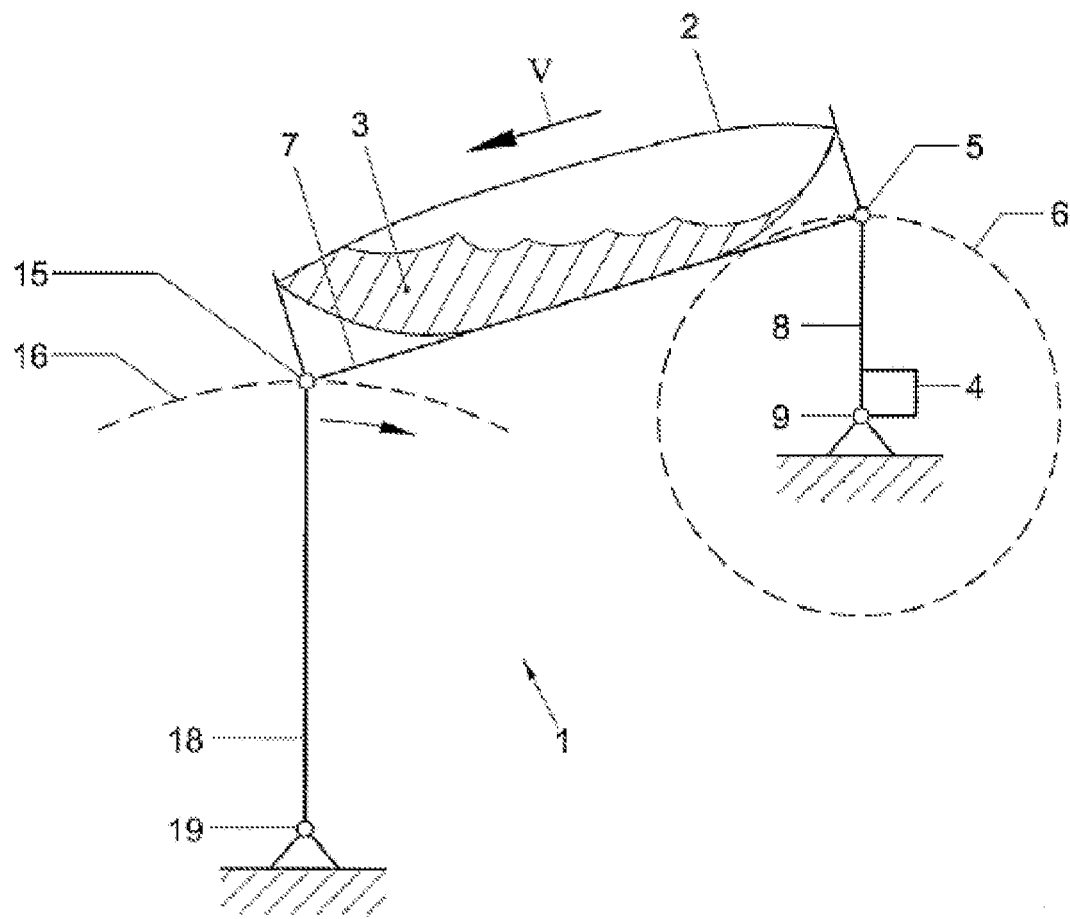
FIG. 1 shows in side view an example of an embodiment of an apparatus according to the invention.
Figure 2A:
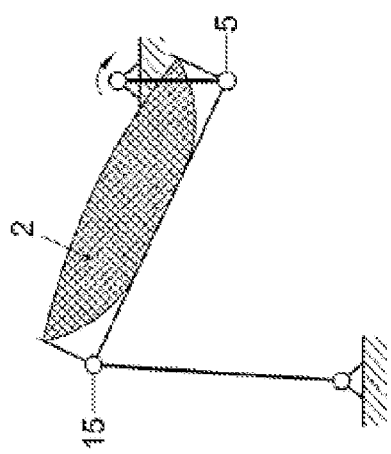
FIGS. 2A-2D show the example of FIG. 1 at different stages during the movement of a container.
Figure 2B:
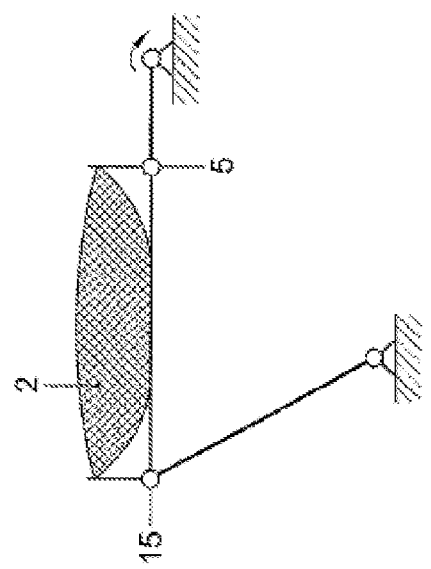
Figure 2C:
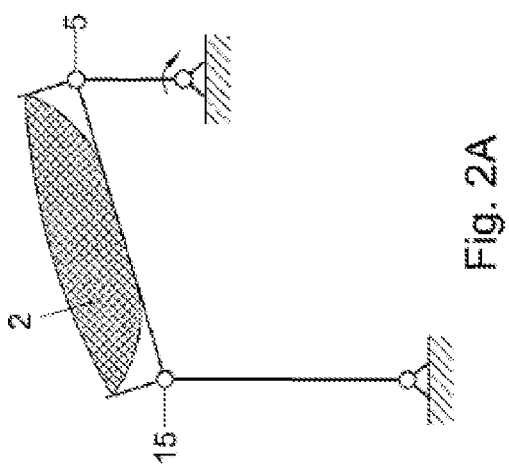
Figure 2D:
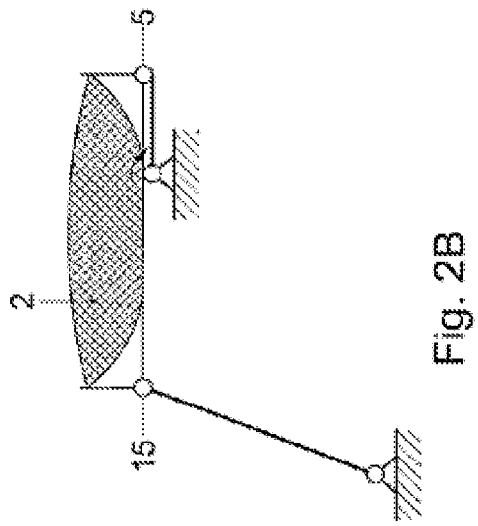

Reference is first made to FIGS. 1 and 2. These figures show an apparatus 1 (bioreactor) for cultivating cells in a container 2 utilizing wave motion of a liquid medium 3 comprising a cell culture in the container. In the shown example, the container 2 is a plastic bag having a single hollow interior chamber. The plastic bag is secured to a platform 7 of the apparatus 1. However, other types of containers and other types of retaining means for retaining the container may also be applied, such as a tray.

The apparatus comprises a driving mechanism for swiveling the platform 7, and hence the bag 2, with respect to a substantially horizontal pivot axis 5. In the example, the pivot axis 5 is the central axis of a hinge joint between the platform 7 and a rotating beam 8 of the apparatus 1. Many types of hinge connections between the platform and the rotating beam 8 can be applied. The rotating beam 8 is driven by a motor 4 to rotate around a rotation axis 9 which is distant and parallel to the pivot axis 5. The driving mechanism is arranged to swivel the bag 2 such that during said swiveling, the pivot axis 5 follows a cyclical closed-loop path 6. The closed-loop path 6 has a circular shape, which is simple to realize. However, by choosing different configurations of the driving mechanism, other shapes of closed-loop paths can be applied as well.

In the example, the platform 7 is furthermore swiveling with respect to a second pivot axis 15 which is distant and parallel to the pivot axis 5. The second pivot axis 15 is the central axis of a second hinge joint between the platform 7 and a second beam 18 of the apparatus 1. The second beam 18 is rotatable with respect to a second rotation axis 19 which is distant and parallel to the second pivot axis 15, such that the second pivot axis 15 of the second beam 18 is free to move back and forth along an arched path 16. The orientation of the first rotation axis 9 relative to the orientation of the second rotation axis 9 remains the same during the movement of the platform.

FIGS. 2A-2D show four different stages during the thus obtained movement of the bag 2.

In the example, the closed-loop path 6 lies in a plane transverse to the pivot axis 5. This is favorable because then the movement vector of the pivot axis along such closed-loop path is in the same plane as the movement vector V of the waves, which turns out to be very efficient. High efficiency is also achieved when at least the projection of the closed-loop path onto a plane transverse to the pivot axis has a closed-loop shape.

However, closed-loop paths can be applied with any type of shape in space, for example a closed-loop path in a horizontal plane through the pivot axis or a closed-loop path in a vertical plane through the pivot axis.

Figure 3:
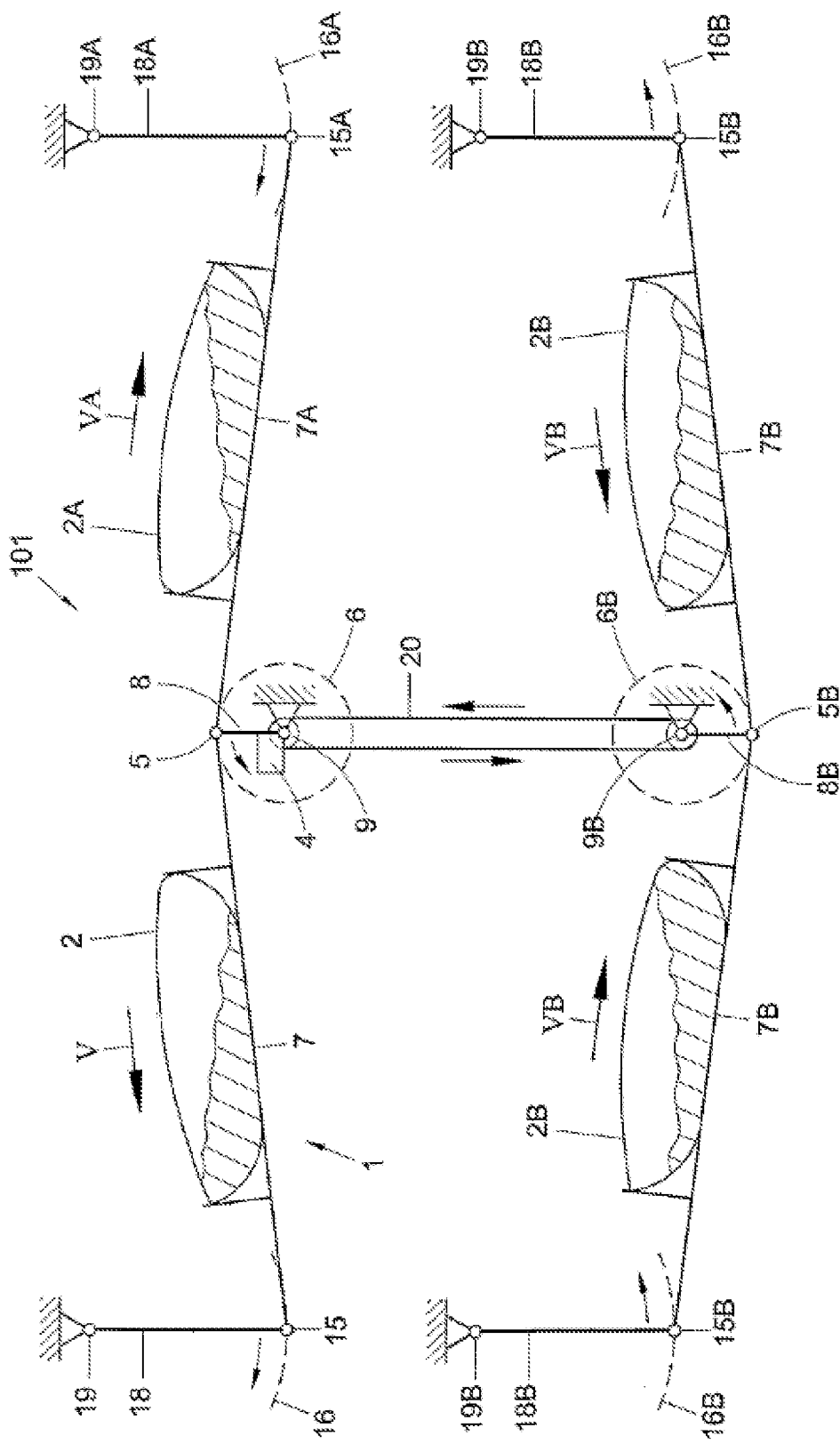
FIG. 3 shows in side view an example of a second embodiment of an apparatus according to the invention.

Reference is now made to FIG. 3, which shows an example of a second embodiment of an apparatus according to the invention. The shown apparatus is an apparatus 101 for cultivating cells in a multiplicity of containers utilizing wave motion of a liquid media. The apparatus 101 comprises an apparatus 1 of the type shown in FIGS. 1 and 2. This apparatus 1 is shown in the upper left part of FIG. 3, wherein the same reference numerals are used as in FIGS. 1 and 2. The apparatus 101 is furthermore arranged for cultivating cells in a co-swiveling container 2A, shown in the upper right part of FIG. 3. For that purpose, the driving mechanism is arranged to swivel both the container 2 and the co-swiveling container 2A simultaneously. In the shown example, this is realized in the following manner.

The co-swiveling bag 2 is retained by a platform 7A, similar to the platform 7 of apparatus 1. This platform 7A has a hinge joint with the rotating beam 8 of apparatus 1, this hinge joint having the pivot axis 5 as central axis.

The platform 7A is furthermore swiveling with respect to a pivot axis 15A which is distant and parallel to the pivot axis 5. The pivot axis 15A is the central axis of a hinge joint between the platform 7A and a beam 18A. The beam 18A is rotatable with respect to a rotation axis 19A which is distant and parallel to the pivot axis 16A, such that the pivot axis 15A of the beam 18A is free to move back and forth along an arched path 16A. The respective orientation of the rotation axes 9 and 19A remains the same during the movement of the platform 7A.

Cultivating cells in a multiplicity of co-swiveling containers simultaneously driven by a joint driving mechanism of an apparatus, offers a number of advantages. For instance, when compared to the use of a larger size single container, once culturing conditions are established for one container, there is no need for additional experimenting to scale up the cell culture volume. All that is required is placing several containers on the apparatus. Furthermore, cell culturing in parallel yet separate containers reduces the risk of culture failures, e.g. by infection or contamination. This contributes to the reliability of the culturing system.

In FIG. 3 the bag 2 and the co-swiveling bag 2A are positioned side by side as seen in a plane transverse to the pivot axis 5. Other types of side by side positions are also possible. For example, a side by side positioning as seen in a vertical plane through the pivot axis 5 is possible, wherein co-swiveling platforms are swiveling relative to the pivot axis 5 at different axial positions along the pivot axis 5.

The apparatus 101 is furthermore arranged for cultivating cells in two co-swiveling containers 2B, shown in the lower left and lower right parts of FIG. 3, respectively. In fact the configuration of the apparatus 101 shown in the upper left and upper right parts of FIG. 3 is repeated in the lower left and lower right parts of FIG. 3. Corresponding parts of the corresponding configurations are denoted by corresponding reference numerals, wherein the affix B is added to the reference numerals, respectively is replacing the affix A of the reference numeral in the upper parts of FIG. 3. In the shown example, this is realized in that the driving mechanism is arranged to swivel both the containers 2 and 2A and the two containers 2B simultaneously, for example by means of a driving belt 20 as shown. Thus, the apparatus 101 is arranged to perform the simultaneous swiveling in a condition in which different swiveling containers are positioned above one another. An advantage of placing a multiplicity of containers above one another is that it reduces costly plant space; the entire assembly of apparatus and containers occupies a much smaller surface area as compared to containers placed adjacent to each other in the horizontal plane. This allows for easy containment of the assembly in a cultivating room.

In the example of FIG. 3, the swiveling direction of the bag 2 relative to the joint pivot axis 5 is opposite to the swiveling direction of the co-swiveling container 2A relative to the joint pivot axis 5. This results into the movement vector V of the waves in the bag 2 and the movement vector VA of the waves in the bag 2A having opposite horizontal components. This turns out to be favorable with respect to energy economy and vibrations of the apparatus in operation.

This also holds for the lower configuration shown in FIG. 3. That is, the swiveling directions of the two shown bags 2B relative to their joint pivot axis 5B are mutually opposite, resulting into movement vectors VB of the waves in the bags 2B having mutually opposite horizontal components. The thus obtained advantage with respect to energy economy and vibrations is enhanced by arranging the apparatus such that the movement vector VB in the lower left part of FIG. 3 has a horizontal component which is opposite to the horizontal component V.

The combined effect of both side by side positioning and positioning above one another of containers, allows two dimensional and three dimensional arrangement of containers in one apparatus. This is favorable with respect to space requirements for carrying out methods for cell cultivation. It also is favorable with respect to costs of apparatuses for cell cultivation, because a single driving structure can be arranged to drive the swiveling motion of many containers.

Figure 4:
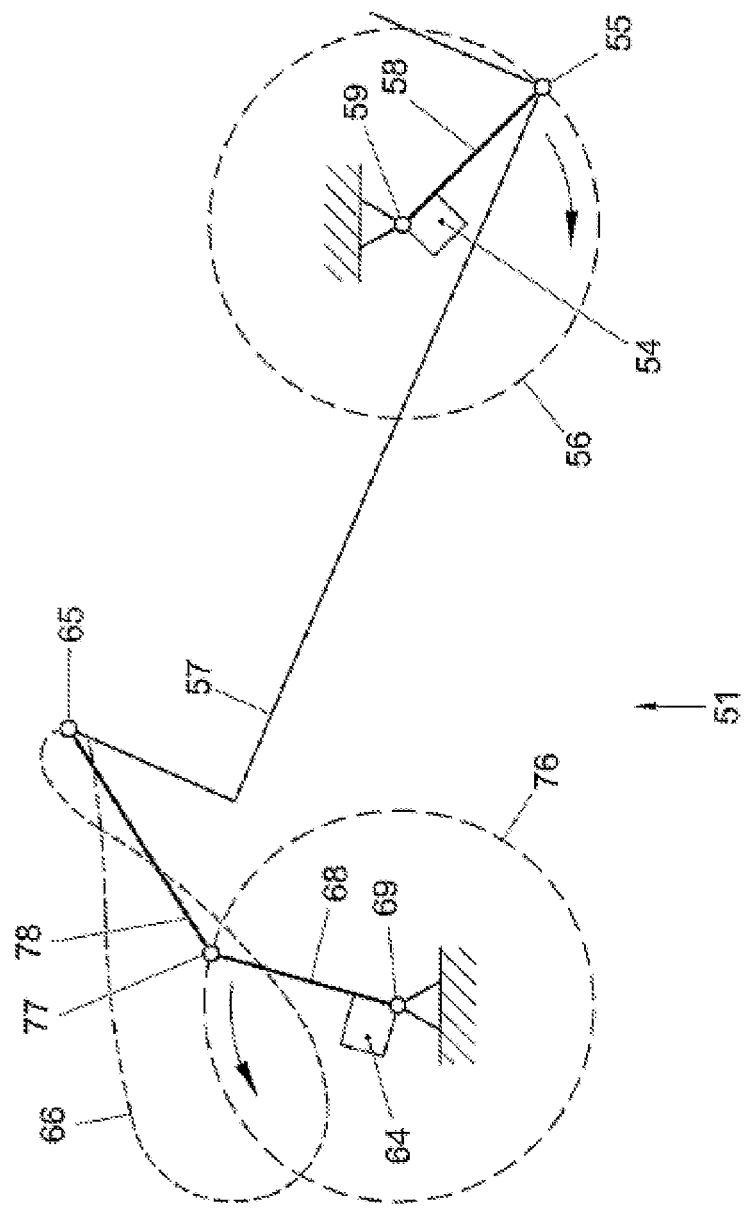
FIG. 4 shows in side view an example of a third embodiment of an apparatus according to the invention.
Figure 6:
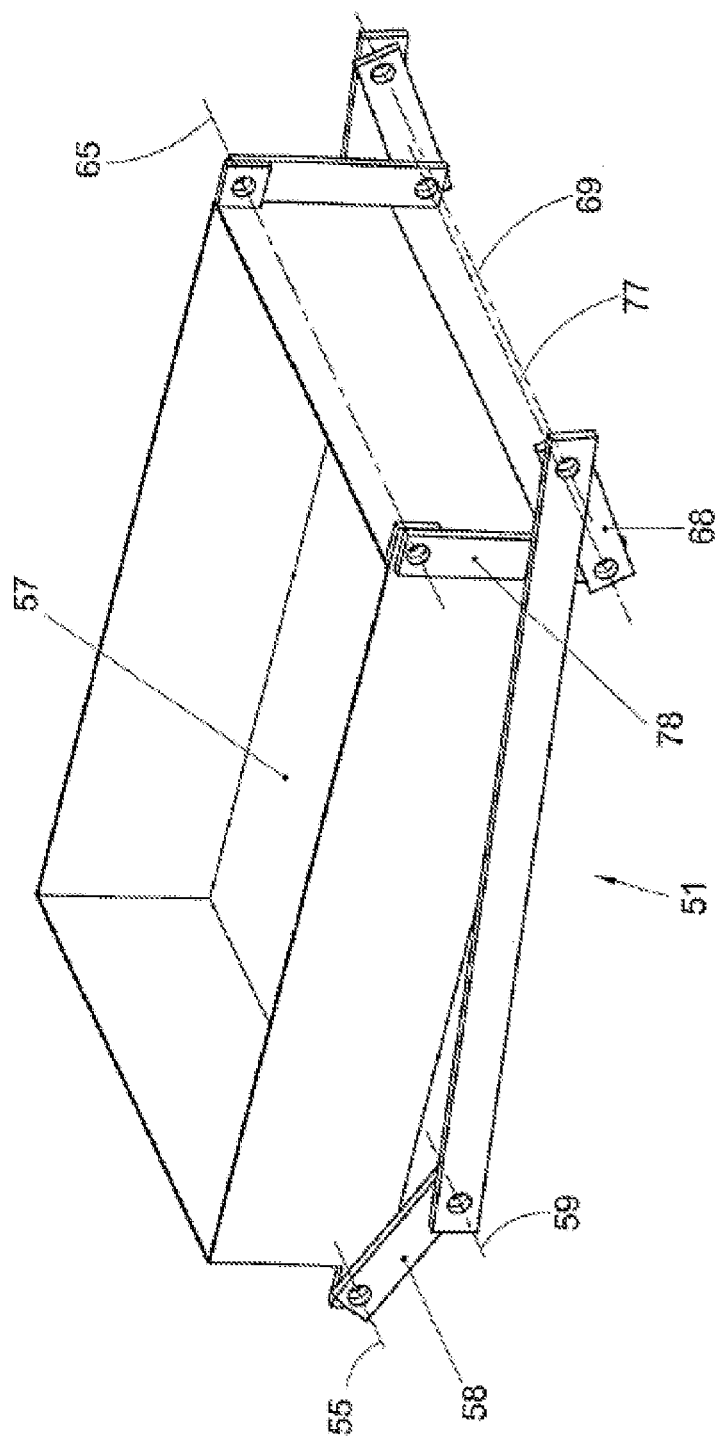
FIG. 6 shows the example of FIGS. 4 and 5 in a perspective view.

Reference is now made to FIGS. 4-6. These figures show an example of a third embodiment of an apparatus according to the invention. The figures show an apparatus 51 for cultivating cells in a container utilizing wave motion of a liquid medium in the container. For reasons of clarity, the container is not shown. Similar to the examples shown in FIGS. 1-3, the container can for example be a plastic bag having a single hollow interior chamber. Such a bag can be secured to the shown platform 57 of the apparatus 51.

Also similar to the examples shown in FIGS. 1-3, the apparatus 51 comprises a driving mechanism for swiveling the container with respect to a substantially horizontal pivot axis 55. In the example, the pivot axis 55 is the central axis of a hinge connection between the platform 57 and a rotating beam 58 of the apparatus 51. The rotating beam 58 is driven by a motor 54 to rotate around a rotation axis 59 which is distant and parallel to the pivot axis 55. The driving mechanism is arranged to swivel the container such that during said swiveling, the pivot axis 55 follows a cyclical closed-loop path 56.

The driving mechanism of the apparatus 51 is furthermore arranged to swivel the container such that during said swiveling the container carries out a second swiveling with respect to a second pivot axis 65 which is distant and parallel to the substantially horizontal pivot axis 55, during which second swiveling the second pivot axis 65 follows a second cyclical closed-loop path 66. The second pivot axis 65 is the central axis of a second hinge connection between the platform 57 and a scissor-beam assembly. In the example, the scissor-beam assembly comprises a second beam 68 and a third beam 78 which beams are interconnected via a hinge axis 77. The second beam 68 is rotatable with respect to a second rotation axis 69 which is distant and parallel to the second pivot axis 65. The rotation of the second beam 68 is driven by a motor 64. During the rotation of the second beam 68, the hinge axis 77 of the scissor-beam assembly follows a cyclical closed-loop path 76 which has circular shape. As an example, FIGS. 4 and 5 show the second cyclical closed-loop path 66 which will be followed by the second pivot axis 65 when the first and second beams 58 and 68 are driven with the same rotation speed, however in opposite rotation directions. The orientation of the first rotation axis 59 relative to the orientation of the second rotation axis 69 remains the same during the movement of the platform 57. It is remarked that, instead of using two motors 54 and 64, also one motor could be applied driving the rotation of both the first beam 58 and the second beam 68, by utilizing suitable transmission means.

An advantage of such an apparatus based upon such second swiveling with respect to a second pivot axis 65 which is distant and parallel to the substantially horizontal pivot axis 55, is that in operation of the driving mechanism a wide range of varying slopes of the container can be obtained with only little vertical space requirement by the driving mechanism. In the example of FIGS. 4-6, only short lengths of the first and second beams 58 and 68 suffice to create such wide slope range. When driving mechanisms such as those described with reference to FIGS. 4-6 are incorporated in apparatuses wherein containers are positioned above one another, such as in the way as described with reference to FIG. 3, said little vertical space requirement will be benefited to an even greater extent.

As already discussed in the introduction, gas-liquid mass transfer is one of the important aspects in the design and operation of bioreactors. The oxygen transfer rate (OTR) depends on the difference between the actual concentration of oxygen in the medium and the maximal achievable concentration of oxygen (saturation concentration) in said medium and a factor $k_l a$ which represents the mass transfer of the gas from the gas-liquid interfacial area in the medium as in the following formula:

$OTR=k_l a(c^*-c)$, where $k_l a$ is the volumetric mass transfer coefficient, $c^*$ is the saturated oxygen concentration, and c is the measured oxygen concentration at a certain time point. The same formula can be drawn up for carbon dioxide transfer. In the experimental section it is shown that the method and the apparatus according to the present invention dramatically increase the $k_l a$, thereby providing for more optimal growth conditions. The experiments also show that application of the method and apparatus of the invention indeed results in increased yields from the cultures, either measured in cell mass or in products (e.g. proteins, such as antibodies) excreted by the cells.

As said, the invention can be practiced using many types of containers. In one embodiment, the container is a disposable container. On completion of the cell cultivation, the cell culture can be simply harvested from the container and the used container is discarded. A new container, provided with a new cell culture, can be immediately placed on the platform of the apparatus. In a preferred embodiment, the container is a pre-sterilized disposable container since this eliminates labor intensive cleaning, sterilization and associated validation. Such containers are known in the art. For example, U.S. Pat. No. 6,190,913 B1 discloses a pre-sterilized flexible plastic bag in which cells are cultivated. These single-use bioreactors are commercially available from Wave Biotech LLC, New Jersey, USA. The container may be provided with additional means, such as means which facilitate the addition or removal of a substance, e.g. liquid medium or a sample, from the container (see for example US2003/0036192).

The invention also relates to a flexible or adjustable cell culturing container. At present, it is common practice to start a cell culture by introducing an inoculation cell culture in a relatively small container comprising a relatively small volume of growth medium, like 200 milliliter, such that the cell density is within an optimal range for cell replication. Subsequently, the starting culture is expanded by a step-wise transfer to containers of increasing size, for example up to a cell culture volume of 20 liters or even more, ensuring that the cell density is maintained within the required range. Presently known containers do not allow to perform the cell culture expansion from a small inoculation culture to a large 'working' culture in one single container. The dimensions of a container that can accommodate the volume of a working culture, e.g. 20 or 30 liter culture, are obviously unsuitable to accommodate the initial starting culture. Each step of the step-wise transfer of a cell culture to a larger container is a critical procedure as it carries the risk of introducing an infection or a contamination into the culture. Furthermore, it is very labor-intensive. To overcome these problems, the invention provides a "flexible" container, that can be compartmentalized and that thus allows for modulating or adjusting the effective volume of the container during cell culturing. The term "effective volume" is meant to indicate the volume of the container which can be occupied by the cell culture. Modulating or restraining the effective volume involves in particular the restraining of one or more flexible walls of the container at the onset of the culturing process, while gradually or stepwise releasing the restrain along with expansion of the cell culture volume. Of course, adjusting the effective volume can also involve reducing the effective volume of the container. As a general rule of thumb, the initial effective volume is about 10% of the maximal volume of the container. Typically, during cell culturing 10 to 80% of the effective volume of the container which, as said, can be adjusted according to the volume of the culture, is filled with liquid medium and cells. There are many ways by which modulation of the effective volume of a container can be realized. The container preferably has one or more flexible walls. It is for example a plastic bag whose side walls can be pushed downwards or towards each other by external means, like clamps, such that the volume of the bag is reduced. A more elegant system is to integrate (one of) the clamps with the disposable container. In this way, the position, which determines the volume, is fixed. With a fixed position, a part of the clamping system could even be used to mount the disposable container on the platform. The clamping system can be integrated with the bag in such a way that the bottom part of the clamps are forming one part with the bottom of the bag. The bottom clamp may, for instance, be glued to the bottom part of the bag. The clamp can be fixed in the supportive tray of the bioreactor system, e.g. by positioning the clamp in a groove in the tray bottom (see FIG. 17B). This figure shows a part of the cross section of a clamped bag, where the bottom side of the clamping system fits within the platform of the bioreactor system.

It is possible to clamp the bag between the clamps in such a way that the bag is closed water tightly at different places before use. For clamping the clamps together different mechanisms may be used: magnetic clamping, mechanical clamping by means of screws or bolts, etc. A person skilled in the art is capable of finding alternative ways to clamp the bag water tightly. The upper side of the clamp can be removed easily to increase the volume. After removal of the upper clamp, the bottom clamp can stay in place, providing for holding the bag in a fixed position in the container.

An alternative for using solid clamps is use of a peal-seal type of closing, in which the seal is integrated in the bag, e.g. as a groove in which a ridge from the opposite side of the bag is clamped. Alternatively, the seal on both sides of the bag consists of weakly adhesive strips. The seal will open by applying pull force from the outside or by applying push force from the inside. In both above mentioned embodiments, mounting a plastic strip on the outside of the bag causes the seal to be closed and to be prevented from opening from inside or outside forces. Removing the strip causes the seal to open by the air and liquid pressure from the internal compartment.

Figure 18:
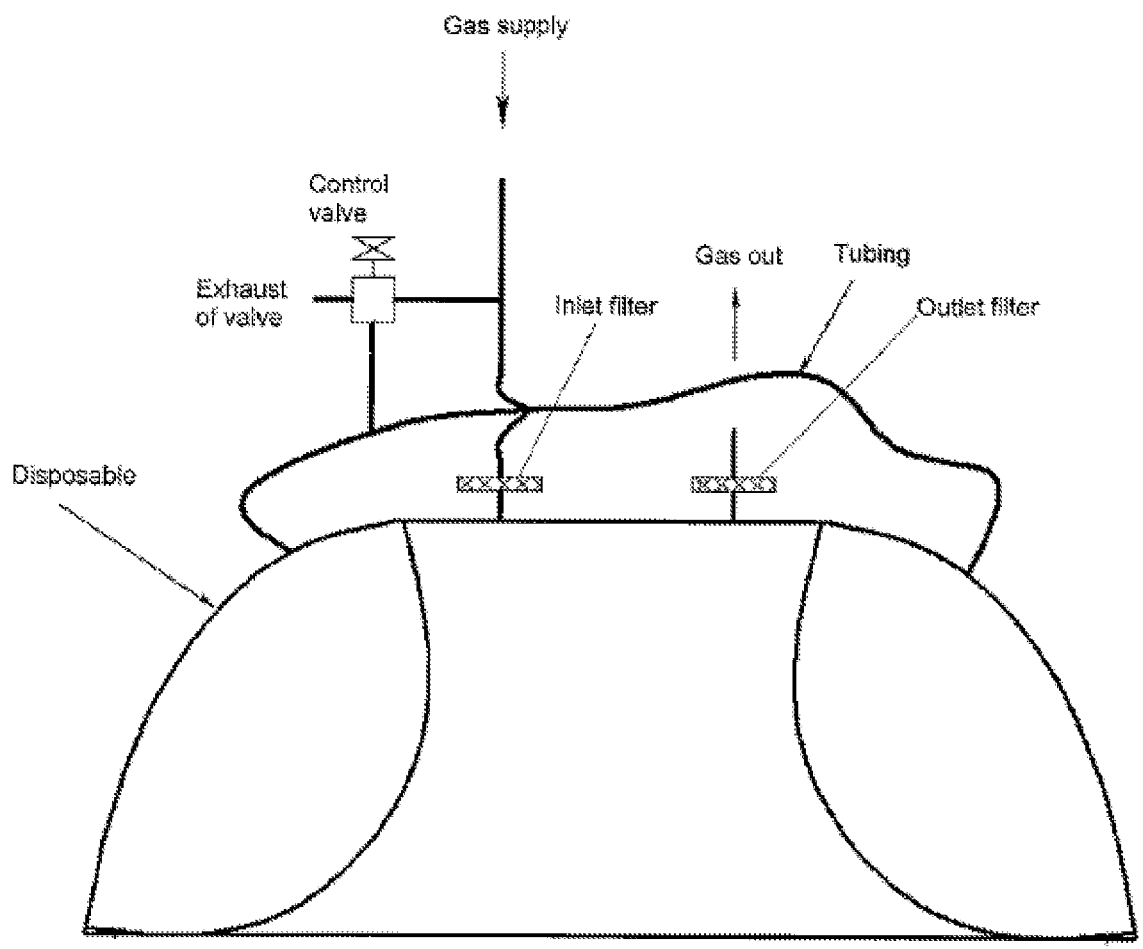
FIG. 18 shows a second embodiment for changing the bioreactor volume of a disposable container. Through a gas inlet the separate compartments on either side of the bag are inflated and thus reduce the volume of the inner (bioreactor) compartment.

Another way to implement a flexible volume system is to use the flexibility of the disposable bag. When on the outside of the bag inflatable compartments are sealed, filling these compartments with gas will decrease the culture volume in the bag. Dependant on the desired volume, these compartments can be (partially) filled and emptied. Due to the pressure provided by these inflatable compartments, controlling of the volume of the container is effected. It is possible to use the gas flow, which normally is led to the container for providing gas to inflate the separate compartments (see FIG. 18). To use the gas supply to control the working volume, the inlet of the gas has to be divided between the compartments to be inflated and the bioreactor. One port goes directly to the inlet filter of the bioreactor, the other port is equipped with a control valve, which controls the opening and closing of the gas flow to the inflatable compartments. In closed position, no gas flows to the inflatable containers, but gas will be present in the bioreactor, thereby forcing the bioreactor to expand to its maximal volume. Opening the valve will inflate the compartments, which then will force the wall of the bioreactor inwards, thereby decreasing the bioreactor volume. Due to the gas outlet of the bioreactor, the pressure inside the inflated chambers will, when the valve is in the open position, always be larger than the pressure within the bioreactor. Releasing gas from the inflated chambers can be performed by using an exhaust switch at the valve.

In all embodiments, it is advantageous to also have a compartmentalization in the heating mats, which are located between the platform support of the apparatus and the container, to allow for differentiated temperature control of the different sections of the container.

Modulating the effective volume of the container during the cell cultivation process by changing the position of at least a flexible part of the container wall can be applied during cell cultivating methods wherein the container is moved in ways as explained above. However, said modulating can also be favorably applied for other cell culturing methods, wherein the container is moved in other ways, or wherein the container is not moved at all.

A third way to increase the working volume of the bioreactor and thereby reaching scale-up of the bacterial or cell culture makes use of an apparatus of the invention which accommodates more than one bioreactor, i.e. more than one container. In this case scale up can be reached by connecting the containers with each other through (disposable) tubing. If a connection between two or more containers is present, a culture can be grown to maximal volume in one container, where after a valve closing off the tubing can be opened, allowing the culture also to occupy a second container. A flow of the content of the container(s) can be exerted by inserting a pump in the tubing. In this way, the more than one container can be characterized as one batch in which the culture has undergone identical process conditions. Preferably, in the case of compartmentalized bioreactors, first the culture is grown in a minimalized bioreactor, then a connection between this reactor and one or more other (minimalized) bioreactors, which have been filled with medium, is established, and then the working volume of all bioreactors is gradually increased (e.g. by removing clamps or by deflating the inflatable compartments). In this way a full scale-up of the culture can be established, from a less than 100 mL culture to cultures of more than 200 L, without the need to repeatedly change containers.

Another important phenomenon is the scale-up strategy based on mass transfer principles. As long as the mass-transfer coefficient $k_La$ is kept the same at different scales the capability of oxygen transfer and $CO_2$-removal will stay the same at the different scales. In such a way the environmental conditions of the cells are the same. In stirred tank reactors and/or bubble columns this is not possible due to the impact of stirrer geometry on for example shear, superficial gas velocity (gasflow/reactor surface) on bubble coalescence and therefore shear damage to the cells and the lower specific liquid surface for surface aeration.

The wave bioreactor (U.S. Pat. No. 6,190,913) is scaled-up into three dimensions (width, length and liquid height of the bag), thereby changing the mass transfer characteristics.

By keeping the wavelength (L) in the bag constant, as well as keeping the rocking speed and the rocking angle the same when scaling-up, the mass transfer characteristics will not change. Important is that the shape of the bag is such that the edges are approx. 90°(+/−15°) (see FIG. 10).

Another approach to keep the mass transfer properties the same in scaling up is to reduce the wavelength but to compensate this by changing the angle as well (at longer wavelengths the angle will decrease). The liquid height should be kept the same, as this mainly determines the specific gas-liquid contact area.

If the angle is changed, the rocking speed should be adjusted as well. This to create the same frequency of the wave. However, the range in between which the rocking speed might be varied, can be large.

Controlling the volume of the container by clamping or otherwise is preferably performed in such a way, that the initial small volume is localized central in the bag. In this way all necessary inlets and outlets can be centrally positioned and accommodate both the bags in minimal volume and in maximal volume. Further, advantageously, the volume in the bag is increased without changing the $k_La$ value. This can be accomplished by causing the volume decreases and increases along with the direction of the wave motion that is made by the bioreactor according to the invention, i.e. parallel to the plane of the container in FIG. 1, see FIG. 17A. Thereby, it is achieved that during increase of the volume, the parameter L, which stands for the wavelength within the container and which influences the $k_La$, remains unchanged.

Figure 17A:
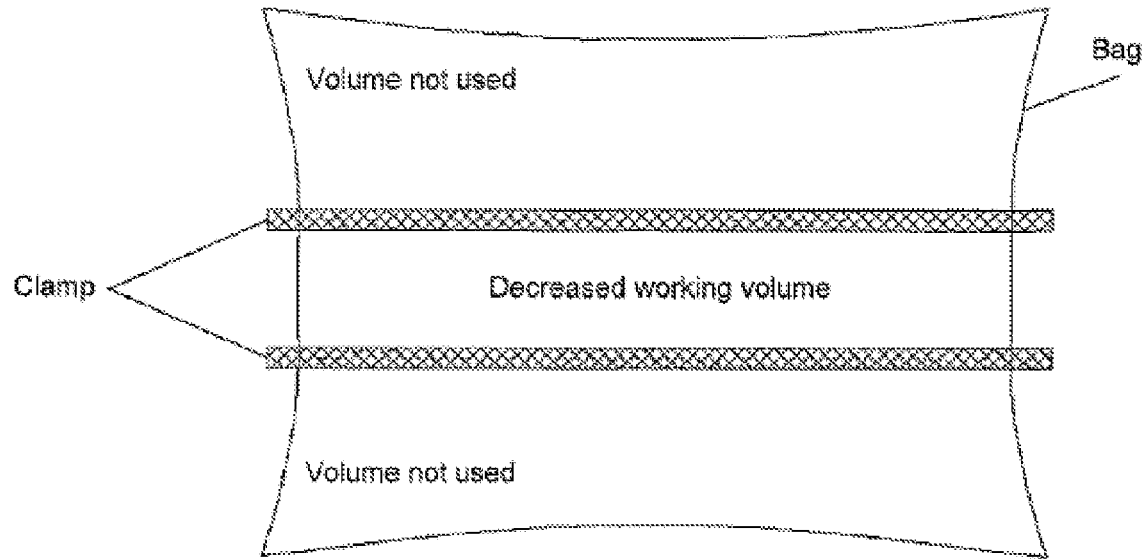
FIG. 17A shows a container with two clamps, whereby reduction of the bioreactor volume can be obtained.
Figure 17B:
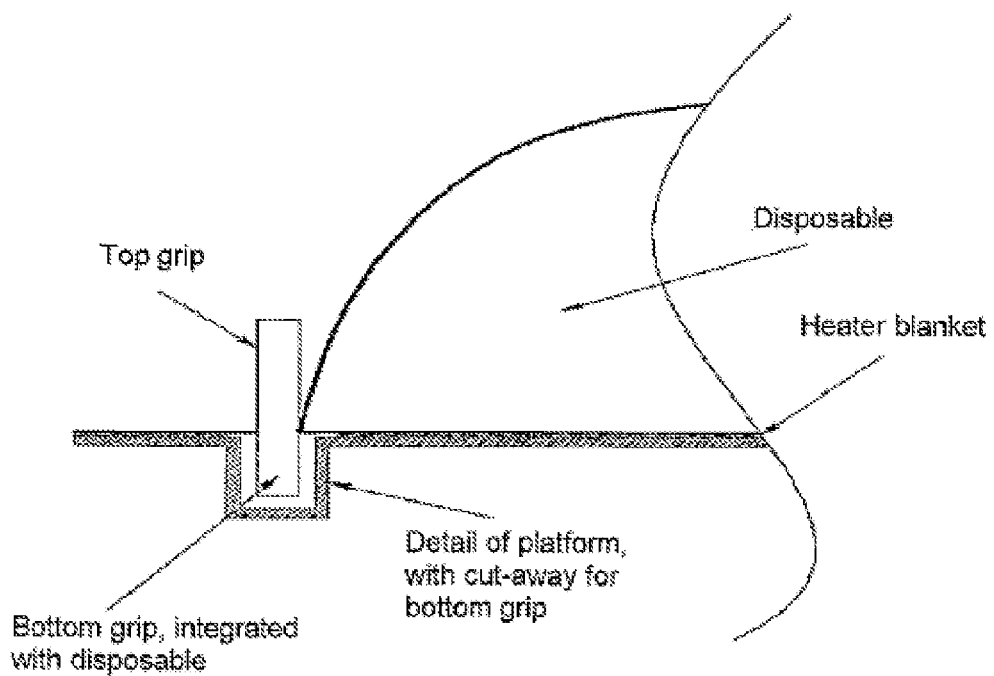
FIG. 17B shows a detail of a possible embodiment for fixating the clamps in the platform support of the disposable container.
Figure 19:
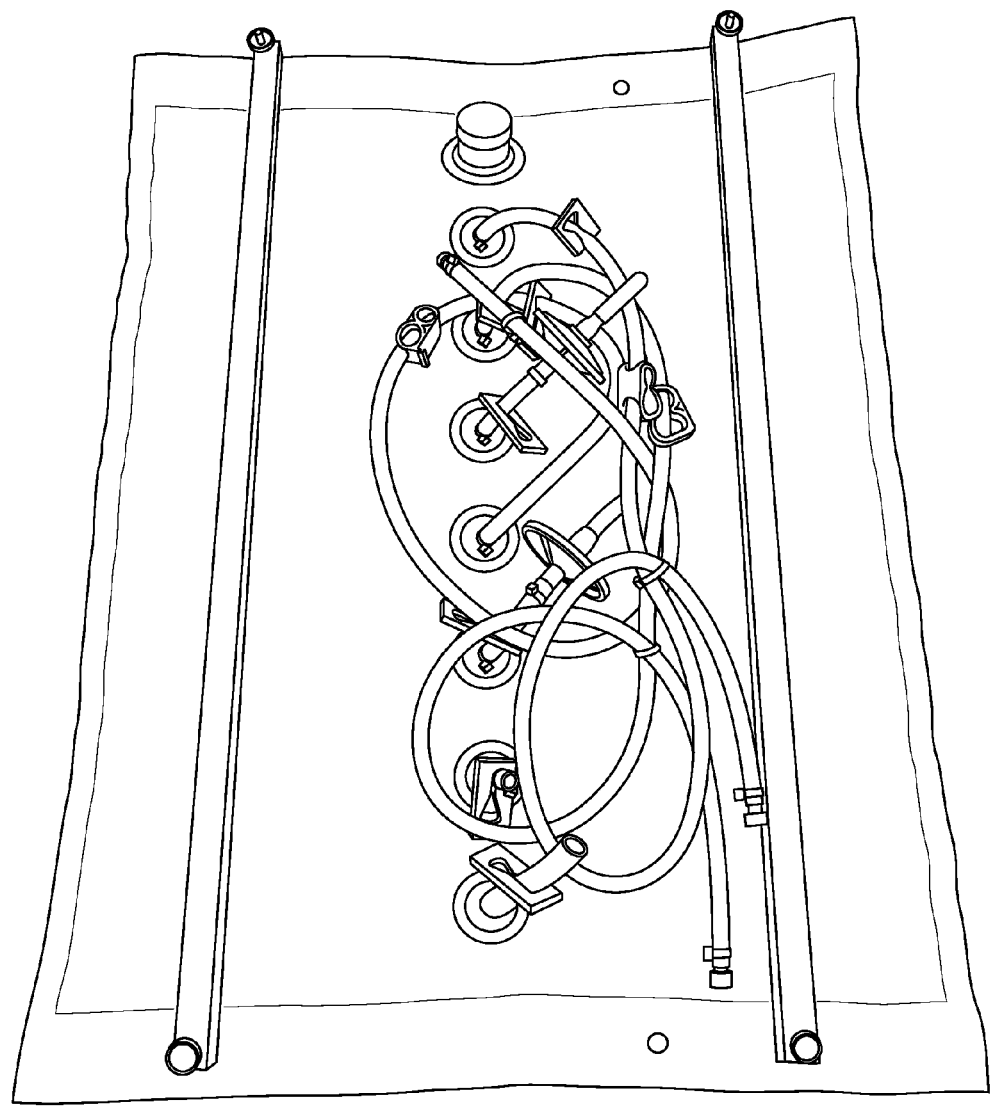
FIG. 19. Example of a container according to the invention.

One example of a bag as schematically depicted in FIG. 17A is depicted in FIG. 19. The position of the clamps is clearly visible, whereby the bag with clamps closed has a working volume of about ½ of the final volume. It will be clear that by adding clamps or taking other positions for the clamps more to the centre of the bag, the initial volume can be decreased. Also the availability of multiple inlets and/or outlets from the bag in the central position should be noted. These inlets and/or outlets can serve as inlet for medium and or inoculum, but also for inlet/outlet of gas (i.e. air or oxygen). Further, as described above, disposable tubing, as is visible in FIG. 19, can be connected to these inlets/outlets to provide for a connection with another bag. Further, the inlets/outlets can be used to take samples from the culture and/or to provide for temperature or other measurements of the culture liquid. Thus, the inlets and/or outlets also provide for coupling with other devices. These devices can be positioned outside the bag or can be integrated with the bag. Such a device can for instance be a pump for providing liquid culture flow between one or more bags, an aeration device, such as a hollow fiber, flat membrane or static mixer, a filter or any other device allowing for isolation of products and/or debris. In this way, e.g. continuous inflow of fresh medium and other essentials for the culture, and continuous outflow of cells and/or products could provide for a continuous culture.

It has also shown that the shape of the container can enhance the effects of the wave motion of the present invention. From Example 1 it can be learnt that the bags ideally would have essentially straight corners, i.e. corners of 90°±20° (see FIG. 10), more preferably corners of 90°±15°, most preferably corners of 90°±10°. Because of the essentially square corners, the wave that is created by the apparatus of the invention 'rocks' against the end of the bag and rolls over its top. Thereby an intense mixing of air and medium is established. When the corners of the bag are rounded off, the wave dies out quickly due to giving the wave a velocity direction towards the middle line of the bag and a less intensive mixing occurs. In all the experiments performed in Example 1, i.e. with different swiveling speeds, different tilt angles and different volumes, the bag with the square corners performed best

EXAMPLES

Example 1 $K_La$ Measurements

Several experiments were done to investigate the actual behavior of the method and the apparatus according to the invention concerning the (oxygen) transfer rate. First these experiments were done with plain tap water as medium, later on a mixture, with physiological properties comparable to real medium, was used.

Experiment

Determination $K_La$-Value

Materials:
"Shocker" apparatus for cultivating cells in a container utilizing wave motion of a liquid medium in the container, comprising retaining means for retaining the container and a driving mechanism for swiveling the container with respect to a substantially horizontal pivot axis, characterized in that the driving mechanism is arranged to swivel the container such that during said swiveling said pivot axis follows a cyclical closed-loop path;
WAVE Cellbag/Applikon media bag;
Presens dissolved oxygen (DO) sensor, transmitter;
$N_2$, compressed air.
Purpose:
Determination of the performance of the Shocker system, concerning the $k_La$-values, by variation of several parameters, like agitation speed and tilt angle.
Operating Procedure:
To calculate the $k_La$-value, the classic dynamic method is used. This means filling the headspace with an inert gas, $N_2$, to drive away the dissolved oxygen in the water.

When the DO-value reads 10% or less, the headspace is filled with air, the machine is started and the DO-value is recorded. After changing the desired parameters the next measurement can start.

After the measurements the DO-values are exported to Microsoft Excel, where the data can be plotted.

With two points of the graph $(C_{L1}, t_1)$ and $(C_{L2}, t_2)$ the $k_La$-value can be calculated with the formula $$k_L \cdot a = \ln\frac{(C_L^* - C_{L1})}{(C_L^* - C_{L2})} \cdot (t_2 - t_1)^{-1},$$

where $(C_{L1}, t_1)$ is the DO-value at time $t_1$, $(C_{L2}, t_2)$ the DO-value at time $t_2$ and $C^*_L$ the saturation concentration (the eventually achieved DO-value).

Plotting the graph on a semi-logarithmic scale will produce a straight line, on which the two points $C_{L1}$ and $C_{L2}$ are chosen.

Hypothesis:

The $k_La$-value is dependent of the exchange area on the interface of liquid and gas. So it will increase for larger fluid displacements, i.e. when agitation speed increases or when the tilt angle increases. It will also increase when the amount of liquid in the bag is reduced due to a lower liquid height (because in the above formula 'a' is the specific mass transfer area=surface/volume).

When the liquid level is increasing however, the wave created is more turbulent and flows back over the topside of the bag. This, at one hand creates a higher "a"-value but on the other hand also a higher $k_L$-value. Such way the mass transfer can increase at bigger volumes. This effect is most strongly at larger rocking speeds.

Figure 7:
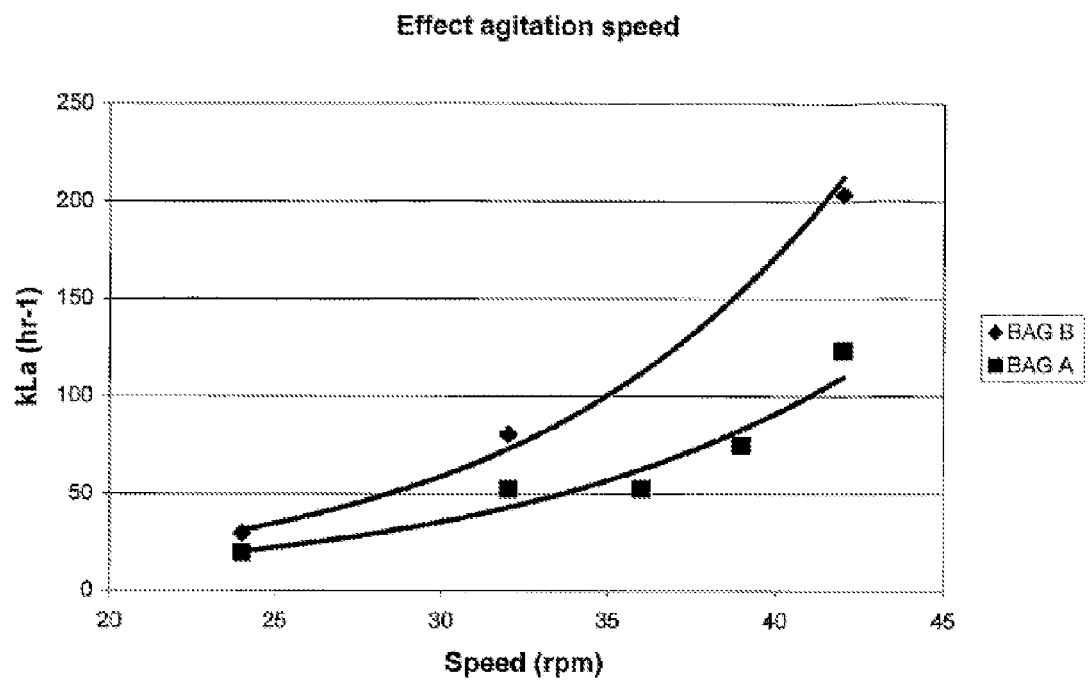
FIG. 7 shows the effects of agitation speed of a bioreactor according to the invention on $k_La$ (volumetric oxygen transfer component) for two different bags A and B (see FIG. 10).
Figure 8:
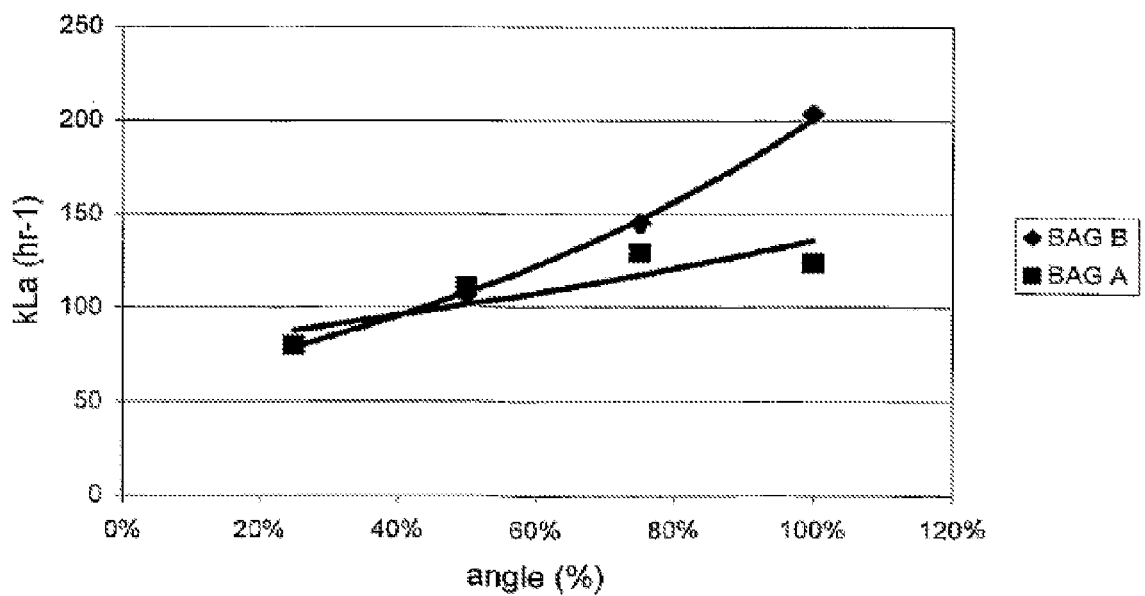
FIG. 8 shows effects of the tilt angle of a bioreactor according to the invention on $k_La$ for two different bags A and B (see FIG. 10).
Figure 9:
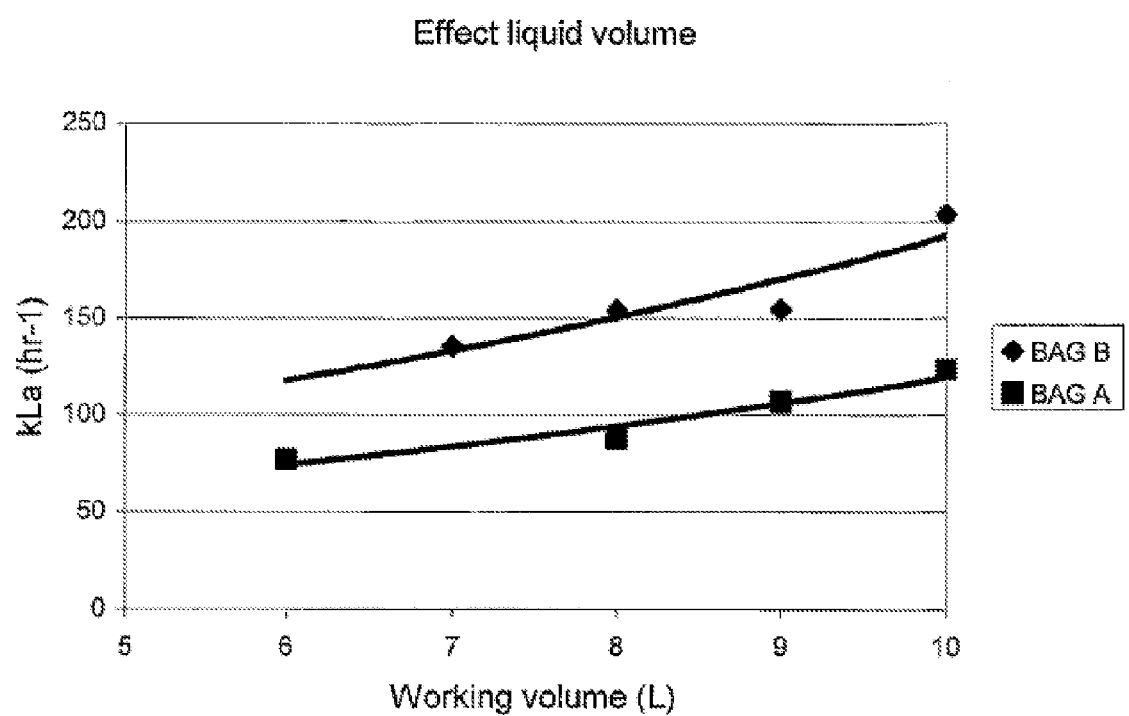
FIG. 9 shows the effect of the liquid volume of a bioreactor according to the invention on $k_La$ for two different bags A and B (see FIG. 10).
Figure 10:
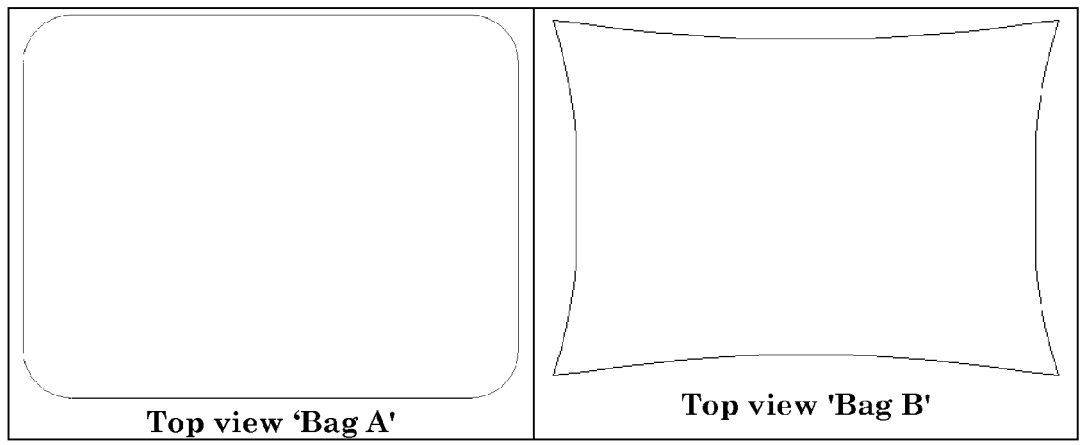
FIG. 10. Schematic representation of the top view shape of bags A and B.

Measurement Results:

Measurements have shown the performance of the system as function of several parameters. These parameters, the agitation speed, the tilt angle and the liquid volume in the disposable were changed while the oxygen concentration in the liquid (water) was measured. With graphing the oxygen concentration against the time it is possible to determine the $k_La$-value with the 'dynamic method'. The results of these experiments are shown in the FIGS. 7-9. During the experiments a distinction is made between the used bags, named "bag A" and "bag B" in the figures. The results show a significant effect on the oxygen transfer characteristics of the different bags. As the size was comparable, just as the amount of liquid during the experiments, the only variable was the shape of the disposables. The top views in FIG. 10 show these differences.

Example 2 Results on Mammalian Cell Cultures

Three different experiments have been performed to investigate the growth and performance of an antibody producing clone of PER.C6®-cells in the apparatus of the present invention (hereinafter also indicated by the name CELL-tainer™).

All the experiments have been performed in commercially available (standard) cultivation bags and standard media and protocols as have been used for PER.C6® cultivation.

The same feed regime (fed-batch) and pre-cultures were used in the comparison experiments.

Experiment 1

Figure 11:
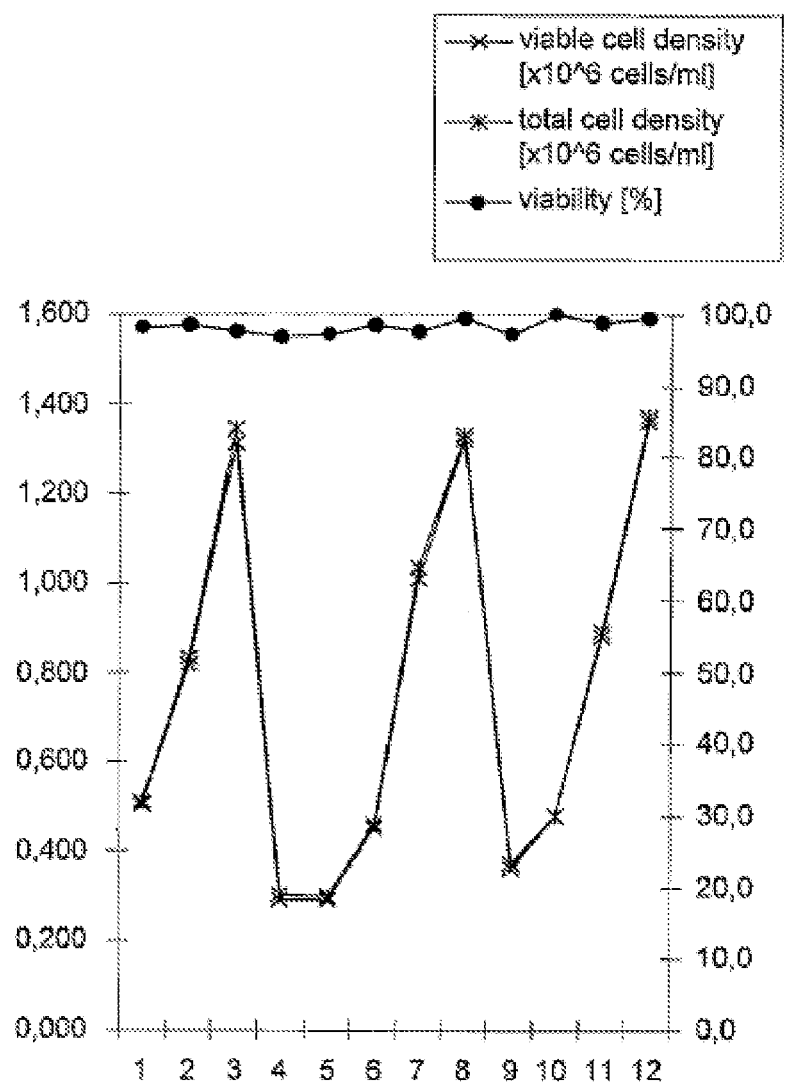
FIG. 11. Viability of PER.C6® cells during pre-culture in a bioreactor according to the invention.

Pre-Culture (See FIG. 11)

After thawing the cells have been kept in pre-culture and the culture has been split two times. The culture has been kept viable during 12 days at viabilities>98%. Conclusion, the CELL-tainer™ can be used for pre-culture.

Experiment 2

Figure 12:
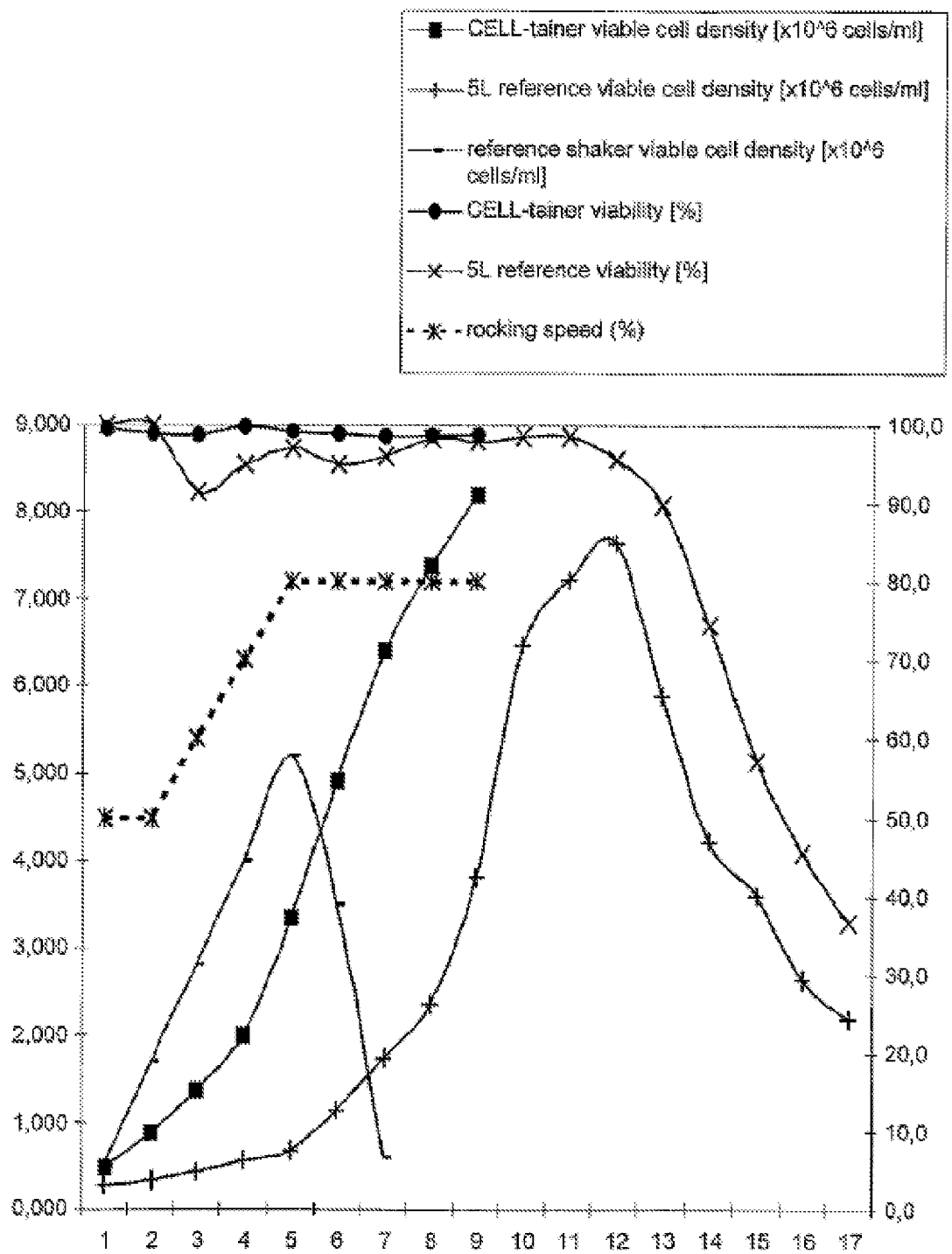
FIG. 12. Viability of PER.C6® cells during batch culture in a bioreactor according to the invention.

Batch Culture (See FIG. 12)

An ordinary batch culture has been performed. Comparison was made with a reference batch culture in a shaker (viable cell density maximum $5 \times 10^6$ cells/ml, blue line), a stirred 5 L bioreactor (viable cell density maximum $7.5 \times 10^6$ cells/ml, green line) and the CELL-tainer™, 10 L working volume (maximum viable cell density $8.0 \times 10^6$ cells/ml).

The viability was kept >98% during the whole experiment which is slightly better than in a stirred bioreactor.

During the experiment, the shaking speed has been increased up to 80% (35 rpm) at the lowest shaking angle showing that the rocking speed does not impact the cells.

Experiment 3

Figure 13:
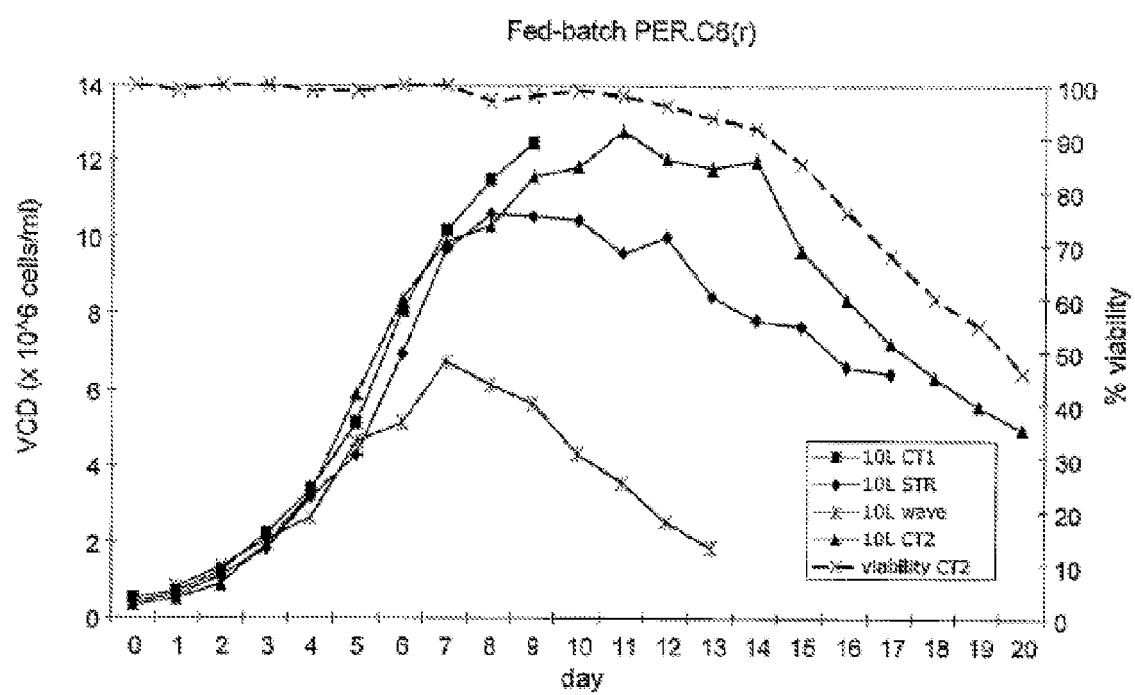
FIG. 13. Viable cell density (VCD) in a fed-batch culture in a bioreactor according to the invention compared to VCD in a traditional stirred bioreactor and a Wave bioreactor.

Fed-Batch Culture (See FIG. 13)

A fed-batch cultivation was performed in the CELL-tainer™ (working volume 10 L) in comparison with a standard 10 L stirred bioreactor, and a 20 L Wave bioreactor (10 L operational volume). During operation of the CELL-tainer™ the overhead space was gassed with a mixed gas, containing 5% $CO_2$. No pH-control has been used. The pH was kept constant due to the buffering capacity of the medium as well as due to the exchange with the overlay gas. Here the performance was different from the STR (stirred bioreactor), where pH-control and stripping of $CO_2$ is needed to keep the pH constant.

The CELL-tainer™ results in a viable cell density (viability>98%) of $13.0 \times 10^6$ cells/ml after eight days (CT1). During day 7-8 of the second run (CT2), there were operational problems with the gas-supply, resulting in a decreased growth during these days.

The STR equipment results in a cell density of approx. $11.0 \times 10^6$ cells/ml after eight days. The Wave bioreactor delivers a maximum of $7.0 \times 10^6$ cells/ml, and growth stops after 7 days.

During the whole experiment, the CELL-tainer™ system was running at 50-70% rocking speed at the minimum angle.

Productivity Data

The production of an IgG type of antibody in the CELL-tainer™ has been compared with that of the production in a traditional stirred bioreactor and a Wave bioreactor.

Figure 14A:
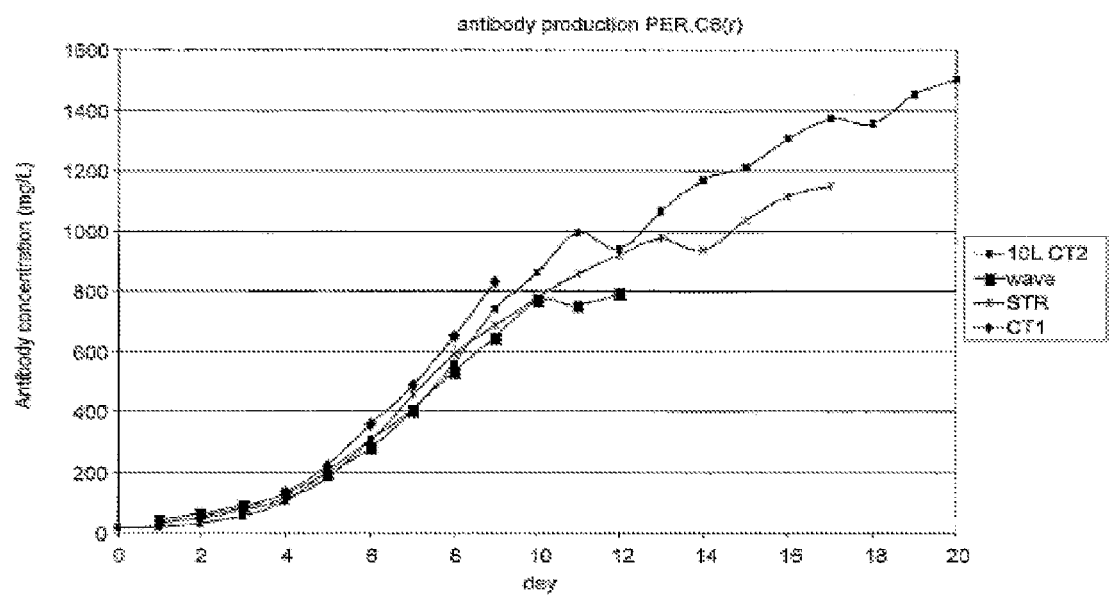
FIG. 14. Production of an IgG type antibody in a fed-batch culture in a bioreactor according to the invention compared to production in a traditional stirred bioreactor and a Wave bioreactor. (A) Antibody concentration versus time of culture. (B) Antibody concentration versus total amount of viable cells produced over time (IVC).
Figure 14B:
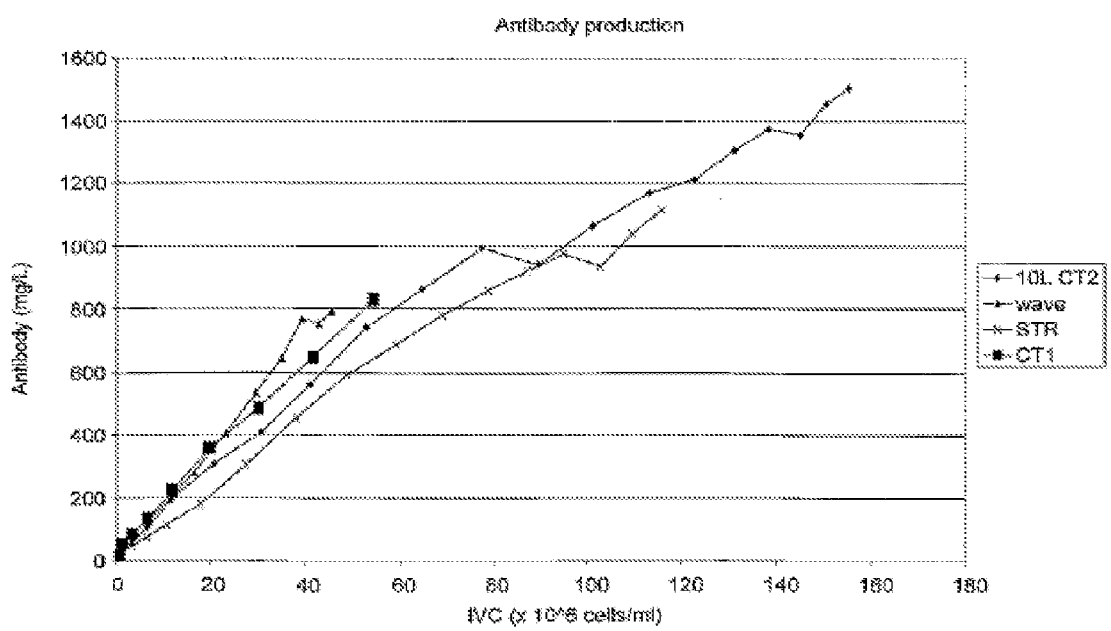

As mentioned above, the cultivation of CT1 has been stopped after eight days. The second experiment in the CELL-tainer™, CT2, resulted in an IVC of $160 \times 10^6$ (cells×day/ml) and a final antibody concentration of 1.5 g/L. (see FIGS. 14A and B)

Example 3

Results on Bacterial Cell Cultures

Materials and Methods

Fermentation

Laboratory experiments were performed in a standard 3.5 L batch stirred bioreactor (Applikon 5 L type Z61100005), with external temperature control (cryostat). The temperature was controlled at 37° C. For growth studies *E. coli* strain EC1000 was used. The medium used was standard TY medium (Trypton (Becton, Dickinson and co.) 1 g/100 ml (1% end conc.); yeast extract (LS ferm powder DSM) 0.5 g/100 ml (0.5% end conc.); sodium chloride (Merck) 0.5 g/100 ml (0.5% end conc.); pH 7.2

Growth was monitored for 24 h by measuring the optical density at 600 nm ($OD_{600}$) on samples of 2-3 ml.

The bioreactor was inoculated with 50 ml preculture shake-flask culture using same media.

RESULTS AND CONCLUSION

Fermentation on TY in a 3.5 L Stirred Bioreactor

Figure 15A:
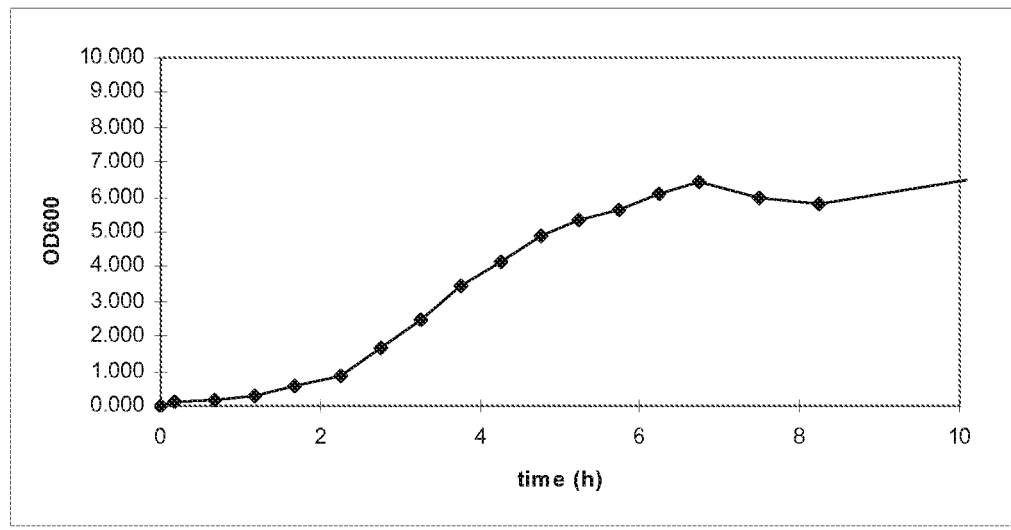
FIG. 15. Growth curve of a bacterial *E. coli* culture in a 3.5 L stirred batch reactor. Cell density measured at $OD_{600}$. (A) Linear Y-axis. (B) Logarithmic Y-axis.
Figure 15B:
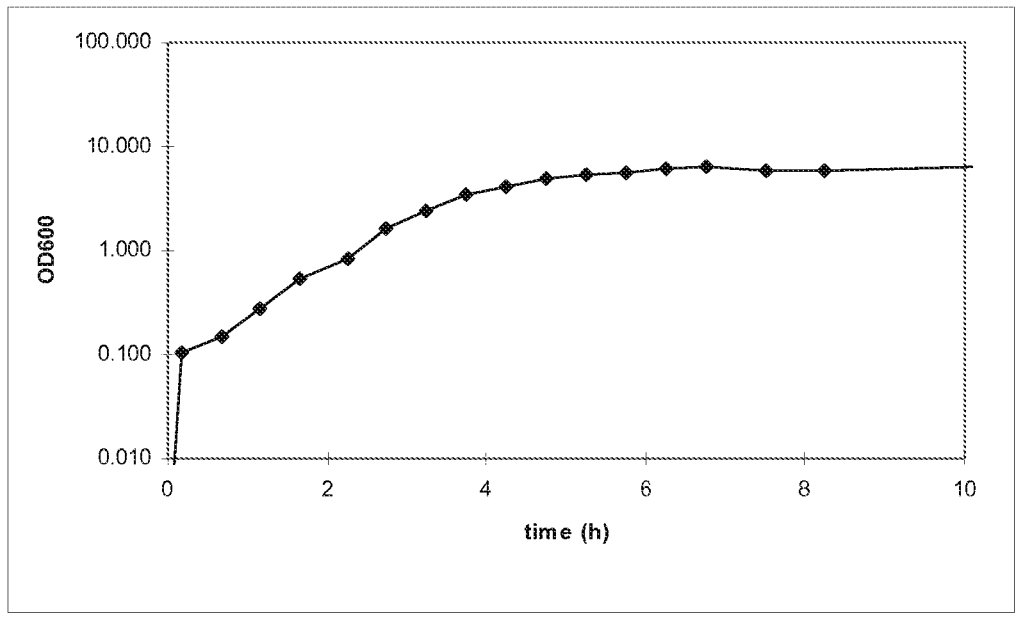

The growth characteristics of the experiments are summarized in Table 1. In FIG. 15 the growth curve is presented, FIG. 15A represents a linear scale of the measured $OD_{600}$ values, FIG. 15B gives the same data on a logarithmic scale.

TABLE 1

Characteristics of fermentation of *E. coli* EC1000 on TY in a stirred bioreactor

| Growth yield ($OD_{600}$) | Max. Growth-rate ($h^{-1}$) |
|---|---|
| 6.5 | 1.4 |

Fermentation on TY in CELL-Tainer™ Compared to a 3.5 STR

Figure 16A:
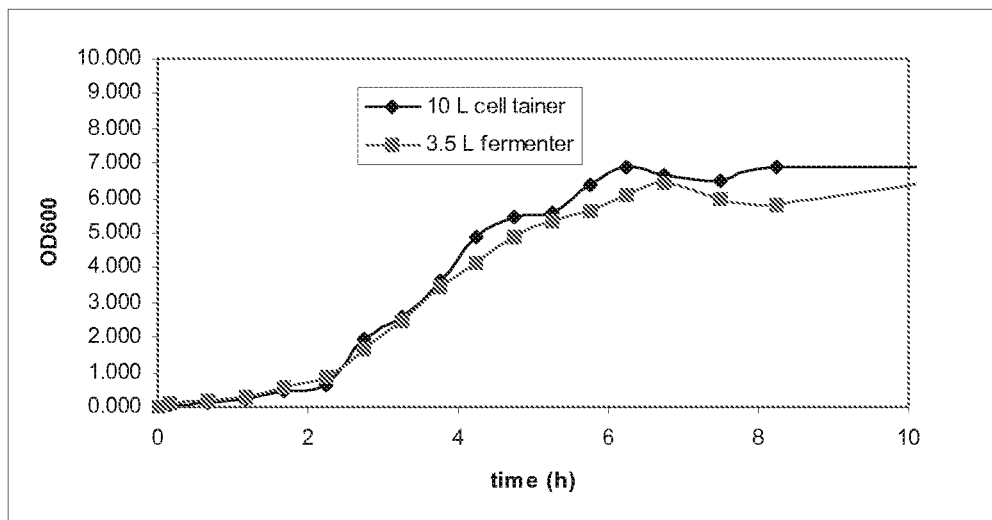
FIG. 16. Comparison of growth curve of a bacterial *E. coli* culture in a 10 L bioreactor according to the invention compared to a 3.5 L stirred bioreactor. (A) and (B) as in FIG. 15.
Figure 16B:
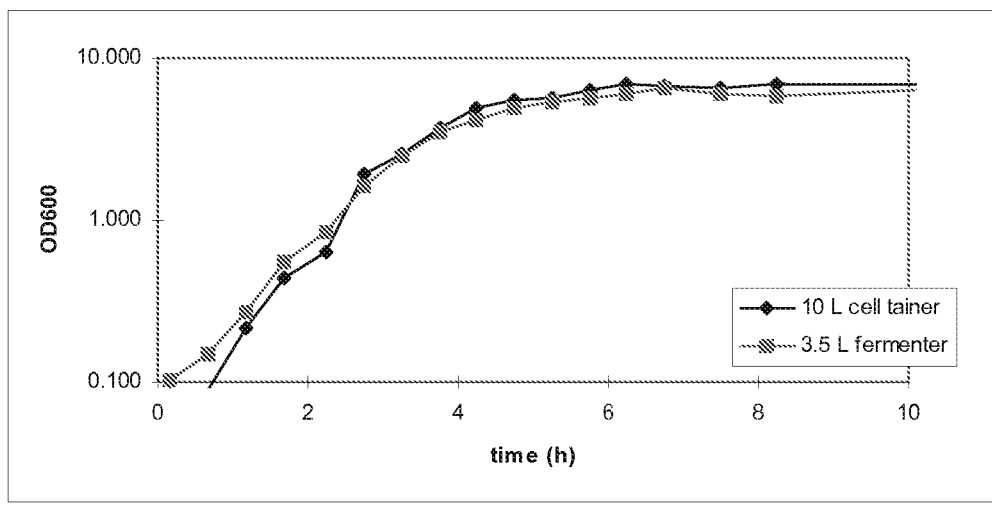

The growth curves and growth characteristics as shown in FIGS. 16A and B and in table 2 were at least similar, some higher maximum growth rate was observed in the CELL-tainer™.

TABLE 2

Characteristics of fermentation of *E. coli* EC1000 on TY in a batch reactor and Cell-tainer ™.

| | Growth Yield ($OD_{600}$) | Max. Growth-Rate ($h^{-1}$) |
|---|---|---|
| Stirred Bioreactor | 6.5 | 1.4 |
| Cell-Tainer ™ | 6.9 | 1.75 |

The invention claimed is:

1. An apparatus for cultivating cells in a container utilizing wave motion of a liquid medium comprising:
   a container for cultivating cells;
   a retaining member configured to retain the container and be positioned and operated above a first plane;
   a substantially horizontal pivot axis about which the retaining member pivots, the substantially horizontal pivot axis extending parallel to the first plane; and
   a drive assembly configured to drive the container with respect to the substantially horizontal pivot axis, wherein the drive assembly is configured to swivel the container such that during said swiveling said substantially horizontal pivot axis follows a cyclical closed-loop path that extends along a second plane, the second plane extending perpendicular to the substantially horizontal pivot axis and perpendicular to the first plane; and
   a movement vector of the substantially horizontal pivot axis along the closed loop path is in a plane that is the same as a movement vector of waves generated in the container when the container is swiveled.

2. The apparatus according to claim 1, arranged for cultivating cells in a co-swiveling container, the drive assembly being arranged to swivel both the container and the co-swiveling container simultaneously.

3. The apparatus according to claim 2, arranged to perform the simultaneous swiveling in a condition in which the container and the co-swiveling container are positioned side by side.

4. The apparatus according to claim 2, arranged to perform the simultaneous swiveling in a condition in which the container and the co-swiveling container are positioned above one another.

5. The apparatus according to claim 2, arranged to perform the simultaneous swiveling such that said substantially horizontal pivot axis functions as joint pivot axis for both the swiveling of the container and the swiveling of the co-swiveling container.

6. The apparatus according to claim 5, arranged to perform the simultaneous swiveling such that the swiveling direction of the container relative to the joint pivot axis is opposite to the swiveling direction of the co-swiveling container relative to the joint pivot axis.

7. The apparatus according to claim 1, arranged for cultivating cells in at least two co-swiveling containers, the drive assembly being arranged to swivel both the container and the at least two co-swiveling containers simultaneously in a condition in which the container and at least one of the at least two co-swiveling containers are positioned side by side and in which the container and at least another one of the at least two co-swiveling containers are positioned one above the other.

8. The apparatus according to claim 1, wherein the driving mechanism drive assembly is arranged to swivel the container such that during said swiveling the container carries out a second swiveling with respect to a second pivot axis which is distant and parallel to the substantially horizontal pivot axis, during which second swiveling the second pivot axis follows a second cyclical closed-loop path.

9. The apparatus according to claim 1, wherein said container is a pre-sterilized, disposable container.

10. The apparatus according to claim 1, wherein the container has an at least partly flexible wall, and wherein the assembly further comprises means for modulating the effective volume of the container during the cell cultivation process by changing the position of at least a flexible part of said wall.

11. The apparatus according to claim 1, wherein the assembly comprises more than one container, which are interconnected.

12. The apparatus according to claim 1, wherein the drive assembly comprises:
   a rotating beam, the retaining member and rotating beam pivoting with respect to one another about the substantially horizontal pivot axis; and a motor configured to rotate the rotating beam around a rotation axis.

* * * * *